US007247305B2

(12) United States Patent
Naparstek et al.

(10) Patent No.: US 7,247,305 B2
(45) Date of Patent: Jul. 24, 2007

(54) AMINO ACID SEQUENCES, DNA ENCODING THE AMINO ACID SEQUENCES, ANTIBODIES DIRECTED AGAINST SUCH SEQUENCES AND THE DIFFERENT USES THEREOF

(75) Inventors: Yaakov Naparstek, Jerusalem (IL); Rina Ulmansky, Jerusalem (IL); Yechezkel Kashi, Haifa (IL)

(73) Assignee: Hadasit Medical Research Services & Development Ltd., Jerusalem (IL)

( * ) Notice: Subject to any disclaimer, the term of this patent is extended or adjusted under 35 U.S.C. 154(b) by 51 days.

(21) Appl. No.: 10/853,567

(22) Filed: May 24, 2004

(65) Prior Publication Data

US 2005/0096285 A1 May 5, 2005

Related U.S. Application Data

(63) Continuation of application No. 09/847,637, filed on May 2, 2001, now Pat. No. 6,770,281, which is a continuation-in-part of application No. PCT/IL99/00595, filed on Nov. 4, 1999.

(60) Provisional application No. 60/107,213, filed on Nov. 5, 1998.

(51) Int. Cl.
*A61K 39/00* (2006.01)
(52) U.S. Cl. .................. 424/185.1; 514/2; 530/326
(58) Field of Classification Search ...................... None
See application file for complete search history.

(56) References Cited

U.S. PATENT DOCUMENTS 5,114,844 A * 5/1992 Cohen et al. .............. 435/7.21
5,780,034 A    7/1998 Cohen et al.
5,985,287 A   11/1999 Tan et al.

FOREIGN PATENT DOCUMENTS

WO    WO 95/25744    9/1995
WO    WO 96/10039    4/1996

OTHER PUBLICATIONS

Wright, HT, 1991, Crit Rev Biochem Mol Biol. 26:1-52.*
McKerrow, JH, 1979, Mech Ageing Dev 10:371-377.*
World wide web.infoplease.com/dictionary/immunity, downloaded Mar. 23, 2006, 2 pages.*
World wide web.onelook.com/?other=web1931&w=Immunity, downloaded Mar. 23, 2006, one page.*
Stryer, L Biochemistry, 4th edition, W.H. Freeman & Co. 1995, pp. 53-58.*
"Amino Acid Side Chain Modification Agents", downloaded from piercenet.com on Mar. 24, 2006, 2 pages.*
"Protein Modification Reagents", downloaded from piercenet.com on Mar. 24, 2006, 4 pages.*
"Cross-Linking", downloaded from piercenet.com on Mar. 24, 2006, 10 pages.*
"Crosslinking Reagents", downloaded from piercenet.com on Mar. 24, 2006, 2 pages.*
The Merck Manual of Diagnosis and Therapy, 17th edition, 1999, editors Beers and Berkow, Merck Research Laboratories, pp. 96-99, 1290-1295, and 1474-1477.*
Colman, P.M., 1994, Research in Immunology, 145:33-36.*
Lopez-Guerrero et al., 1993, Infection and Immunity, 61:4225-4231.*
The Merck Manual of Diagnosis and therapy, 17th edition, Merck Resaerch Laboratories, 1999, pp. 416-423, 922-925, and 1496-1499.*
Astarloa et al., J. Neurological Sciences, 1996 135:182-183.*
Xiao et al., BMC Blood Disorders, 2004, 4:1, 10 pages.*
Janeway et al., Immunobiology, 3rd edition, Garland Publishing Inc, 1997, pp. 8:2-8:7.*
Jordan et al., Clin exp Immunol 1994, 97 suppl 1:31-38.*
Anderton et al., "Inflammation activates self hsp60-specific T. cells", Eur. J. Immuno., 23:33-38, 1993.
Anderton et al., "Activation of T Cells Recognizing Self 60-kD Heat Shock Protein Can Protect against Experimental Arthritis", J. Exp. Med., 181:943-952, 1995.
Anderton et al, "Differential mycobacterial 65-kDa Heat Shock Protein T. Cell Epitope Recognition after Adjuvant Arthritis-Inducing or Protective Immunization Protocols", Journal of Immunology, 152:3656-3664, 1994.
Barker et al., "Differential Effects of Immunization with Mycobacterial 65 kD Heat Shock Protein on Two Model of Autoimmunity", Immunity, 14:73-77, 1992.
Billingham et al, "a Mycobacterial 65-kD heat Shock Protein Induces Antigen-Specific Suppression Of Adjuvant Arthritis, But Is Not Itself Artritogenic", J. Exp. Med. 171:339-344,1990.
Chen et al., "Human 60-kDa Heat-Shock Protein: A Danger Signal to the Innate Immune System", The Journal of Immunology, 162:3212-3219, 1999.
Elias, D. and Cohen, Ir, "The hsp60 Peptide p277 Arrests the Autoimmune Diabetes Induced by the Toxin Streptozotocin" Diabetes, 45:1168-1172, 1996.
Elais, D. and Cohen, Ir, "Peptide therapy for diabetes in NOD mice", The Lancet, 343:704-706, 1994.
Freidland et al, "Mycobacterial 65-kD heat shcok protein induces release of proinflammatory cytokines from human monocytic cell", Clin Exp. Immunol, 91:58-62, 1993.
Ghoraishian et al, "Comparison between the protective effects of mycobacterial 65-kD heat shock protein and ovomucoid in pristane-induced arthritis: relationship with agalactosyl lgG", Clin. Exp. Immunol., 94:247-251, 1993.

(Continued)

*Primary Examiner*—Christina Chan
*Assistant Examiner*—Michael Szperka
(74) *Attorney, Agent, or Firm*—Martin Fleit; Paul D. Bianco; Fleit Kain Gibbons Gutman Bongini & Bianco P.L.

(57) ABSTRACT

The invention is directed to a peptide comprising the amino acid sequence substantially as denoted by SEQ ID NO:1 and biologically functional homologues and derivatives thereof.

3 Claims, 7 Drawing Sheets

OTHER PUBLICATIONS

Griffiths et al., "Induction of Autoimmune Arthritis in Rats by Immunization with Homologous Rat Type II Collagen is Restricted to the RT1av1 Haplotype", Arthritis and Rheumatism, 36(2):254-258, 1993.

Henwood et al, "Restricted T Cell receptor expression by human T cell clones specific for mycoobacterial 65-kDa heat-shock protein: selective in vivo expansion of T cells bearing defined receptors", Eur. J. Immunol., 23:1256-1265, 1993.

Hill Gaston et al, "Recognition of a mycobacteria-Specific Epitope in the 65 kD Heat-Shock Protein by Synovial Fluid-Derived T Cell Clones", J. Exp. Med., 171:831-841, 1990.

Hill Gaston et al, "In Vitro Responses to a 65-Kilodatton Mycobacterial Proteins by Synovial T. Cells from Inflammatory Arthritis Patients", The Journal of Immunology, 143(8):2494-2500, 1989.

Hogervorst et al, "Modulation of Experimental Autoimmunity: Treatment of Adjuvant Arthritis by Immunization with Recombinat Vaccinia Virus", Infection and Immunity, 59(6):2029-2035, 1991.

Hogervorst et al., "T cell reactivity to an epitope of the mycobacterial 65-kDa heat-shock protein (hsp 65) corresponds with arthritis susceptibility in rats and is regulated by hsp 65-specific cellular responses", J. Immunol. 21:1296, 1991.

Holoshitz et al., T Lymphocytes of Rheumatoid Arthritis Patients Show Augmented Reactivity to a Fraction of Mycobateria Cross-Reactive with Cartilage, The Lancet, 305-309, 1986.

Holoshitz et al, "Lines of T Lymphocytes Induce or Vaccinate Against Autoimmune Arthritis" Science, 219:56-58, 1983.

Jindal et al, "Primary Structure of a Human Mitochondrial Protein Homologous to the Bacterial and Plant Chaperonins and to the 65-Kilodalton mycobacterial Antigen", Molecular and Cellular Biology, 9 (5):2279-2283, 1989.

Jordan, SC and Toyoda, M, "Treatment of autoimmune diseases and systemic vasculitis with pooled human intravenous immune globulin", Clin. Exp. Immunol., 97(1):31-38, 1994.

Kasprzyk et al, "Solid-Phase peptide Quantitation Assay Using Labeled Monoclonal Antibody and Glutaraldehyde Fixation", Analytic Biochemistry, 174:224-234, 1988.

Kleinau et al, "A Monoclonal Antibody to the Mycobacterial 65kDa Heat Shock Protein (ML 30) Binds to Cells in Normal and Arthritic Joints of Rats", Scand. J. Immunol., 33:195-202, 1991.

Lopez-Mortalla et al, "A common structural motif in immunopotentiating peptides with sequences present in human autoantigens. Elicitation of a response mediated by monocytes and Th 1 cells", Biochemica et Biophysica acta, 1317:183-191, 1996.

Maloy et al, "Production of Antipeptide Antisera", Current Protocols in Immunology, 39:9.4-9.4.12, 2000.

Margulies, DH, "Antibody Detection and Preparation", Current Protocols in Immunology, 2.01-1.13.16, 1996.

Moudgil et al., "Diversification of T Cell Responses to Carboxy-terminal Determinants within the 65-kD Heat-Shock Protein is Involved in Regulation of Autoimmune Arthritis", J. Exp. Med., 185(7):1307-1316, 1997.

Munk et al., "T Lymphocytes from Healthy Individuals with Specificity to Self-Epitopes Shared by the Mycobacterial And Human 65-Kilodalton Heat Shock Protein", The Journal of Immunology, 143(9):2844-2849, 1989.

Pearson, Carl M., "Development of Arthritis, periarthritis and Perlostitis in Rats Given Adjuvants", Proc. Soc. Exp. Biol. Med. 91:95-100 (1956).

Pearson, Carl M. and Wood, Fae D., "Studies of Polyarthritis and Other Lesions Induced in Rats by Injection of Mycobacterial Adjuvant. I. General Clinical and Pathologic Characteristics and Some Modifying Factors", Arthritic Lesions from Mycobacteria, 2:440-450 (1956).

Prakken et al., "Nasal administration of arthritis-related T cell epitopes of heat shock protein 60 as a promising way for immunotherapy in chronic arthritis", Biotheraphy, 10:205-211, 1998.

Prakken et al, "Peptide-induced nasal tolerance for a mycobacterial heat shock protein 60 T cell epitope in rats suppresses both adjuvant arthritis and nonmicrobially induced experimental arthritis", Proc. Natl. Acad. Sci. USA, 94:3284-3289, 1997.

Qauyle et al, "peptide recognition, T cell receptor usage and HLA restriction elements of human heat-shcok protein (hsp) 60 and mycobacterial 65-kDa hsp-reactive T cell clones from rheumatoid synovial fluid", Eur. J. Immunol., 22:1315-1322, 1992.

Res et al., "Synovial Fluid T Cell Reactivity Against 65 kD Heat Shock Protein of Mycobacteria in Early Chronic Arthritis", The Lancet, 478-480, 1988.

Ulmansky, R. and Naparstek, Y., "Immunoglobulins from rats that are resistant to adjuvant arthritis suppress the disease in arthritis-susceptible rats", Eur. J. Immunol. 25:952-957, 1995.

van Eden et al., "Cloning of the mycobacterial epotope recognized by T lymphocytes in adjuvant arthritis", Nature, 331:171-173, 1988.

Waksman, BH and Wennersten, C, Passive Transfer of Adjuvant Arthritis in Rats with Living Lymphoid Cells of Sensitized Donors, Int. Arch. Allergy, 23(3-4):129-139, 1963.

Warren et al, "Fine Specificity of the antibody response to myelin basic protein in the central nervous system in multiple sclerosis: The minimal B-cell epitope and a model of its features", Proc. Natl. Acad. Sci. USA, 92:11061-11065, 1995.

Yang et al., Prevention of adjuvant arthritis in rats by a nonapeptide from the 65-kD mycobacterial heat-shock protein, Clin. Exp. Immunol., 81:189-194, 1990.

Yang et al, "Treatment of Adjuvant Arthritis in Rats: Vaccination Potential of a Synthetic Nonapeptide from the 65 kDa Heat Shock Protein of Mycobacterial", Journal of Autoimmunity, 3:11-23, 1990.

Lederman et al, Molecular Immunology, vol. 28, No. 11, pp. 1171-1181 (1991).

Hogervorst et al., Adjuvant arthritis and immunity to the mycobacterial 65 kDa heat shock protein, International Immunology, 4(7):719-727,1992.

Li et al. Proc. Natl. Acad. Sci.USA, vol. 77, No. 6, pp. 3211-3214, (1980).

Van Regenmortel Marc H.V., Methods: "A Companion to Methods of Enzymology", vol. 9, pp. 465-472, (1996).

* cited by examiner

```
                                              1         6                25
HSP 65 - M.T.   ---------- ----------- ------MAKTI AYDEEARRGL ERGLNALADA
HSP 60 - RAT    MLRLPTVLRQ MRFVSRALAP HLTRAYAKDV KFGADARALM LQGVDLLADA
HSP 60 - HUMAN  MLRLPTVFRQ MRFVSRVLAP HLTRAYAKDV KFGADARALM LQGVDLLADA

Consensus       ---------- ---------- ------AK-- ------AR--- --G---LADA 26                                                    75
HSP 65 - M.T.   VKVTLGPKGR NVVLEKKWGA PTITNDGVSI AKEIELEDPY EKIGAELVKE
HSP 60 - RAT    VAVTMGPKGR TVIIEQSWGS PKVTKDGVTV AKSIDLKDKY KNIGAKLVQD
HSP 60 - HUMAN  VAVTMGPKGR TVIIEQSWGS PKVTKDGVTV AKSIDLKDKY KNIGAKLVQD Consensus       V-VT-GPKGR -V--E--WG- P--T-DGV-- AK-I-L-D-Y --IGA-LV--
                     6-7(31-52 AA)

76                                                    125
HSP 65 - M.T.   VAKKTDDVAG DGTTTATVLA QALVREGLRN VAAGANPLGL KRGIEKAVEK
HSP 60 - RAT    VANNTNEEAG DGTTTATVLA RSIAKEGFEK ISKGANPVEI RRGVMLAVDA
HSP 60 - HUMAN  VANNTNEEAG DGTTTATVLA RSIAKEGFEK ISKGANPVEI RRGVMLAVDA

Consensus       VA--T---AG DGTTTATVLA -----EG--- ---GANP--- -RG---AV--
                                                                21 (121-136 AA)

126                                                   174
HSP 65 - M.T.   VTETLLKGAK EVETKEQIAA TAAISA.GDQ SIGDLIAEAM DKVGNEGVIT
HSP 60 - RAT    VIAELKKQSK PVTTPEEIAQ VATISANGDK DIGNIISDAM KKVGRKGVIT
HSP 60 - HUMAN  VIAELKKQSK PVTTPEEIAQ VATISANGDK EIGNIISDAM KKVGRKGVIT

Consensus       V---L-K--K -V-T-E-IA- -A-ISA-GD- -IG--I--AM -KVG--GVIT 175                                                   224
HSP 65 - M.T.   VEESNTFGLQ LELTEGMRFD RGYISGYFVT DPERQEAVLE DFYILLVSSK
HSP 60 - RAT    VKDGKTLNDE LEIIEGMKFD RGYISPYFIN TSKGQKCEFQ DAYVLLSEKK
HSP 60 - HUMAN  VKDGKTLNDE LEIIEGMKFD RGYISPYFIN TSKGQKCEFQ DAYVLLSEKK Consensus       V-----T---- LE--EGM-FD -GYIS-YF-- ----Q----- D-Y-LL---K
                           31 (181-196 AA)              36 (211-226 AA)

225                                                   274
HSP 65 - M.T.   VSTVKDLLPL LEKVIGAGKP LLIIAEDVEG EALSTLVVNK IRGTFKSVAV
HSP 60 - RAT    ISSVQSIVPA LEIANAHRKP LVIIAEDVDG EALSTLVLNR LKVGLQVVAV
HSP 60 - HUMAN  ISSIQSIVPA LEIANAHRKP LVIIAEDVDG EALSTLVLNR LKVGLQVVAV

Consensus       -S------P- LE------KP L-IIAEDV-G EALSTLV-N- -------VAV
                           40 (236-251 AA)              45 (265-280 AA)
```

Fig. 1

```
                    275                                                           323
HSP 65 - M.T.       KAPGFGDRRK AMLQDMAILT GGQVISEE.V GLTLENADLS LLGKARKVVV
HSP 60 - RAT        KAPGFGDNRK NQLKDMAIAT GGAVFGEEGL NLNLEDVQAH DLGKVGEVIV
HSP 60 - HUMAN      KAPGFGDNRK NQLKDMAIAT GGAVFGEEGL TLNLEDVQPH DLGKVGEVIV

Consensus           KAPGFGD-RK --L-DMAI-T GG-V--EE-- -L-LE----- -LGK---V-V 324                                                           373
HSP 65 - M.T.       TKDETTIVEG AGDTDAIAGR VAQIRQEIEN SDSDYDREKL QERLAKLAGG
HSP 60 - RAT        TKDDAMLLKG KGDKAHIEKR IQEITEQLDI TTSEYEKEKL NERLAKLSDG
HSP 60 - HUMAN      TKDDAMLLKG KGDKAQIEKR IQEIIEQLDV TTSEYEKEKL NERLAKLSDG Consensus           TKD-------G -GD---I--R ---I------ --S-Y--EKL -ERLAKL--G
                                                        |59 (349-364 AA)|

374                                                           423
HSP 65 - M.T.       VAVIKAGAAT EVELKERKHR IEDAVRNAKA AVEEGIVAGG GVTLLQAAPT
HSP 60 - RAT        VAVLKVGGTS DVEVNEKKDR VTDALNATRA AVEEGIVLGG GCALLRCIPA
HSP 60 - HUMAN      VAVLKVGGTS DVEVNEKKDR VTDALNATRA AVEEGIVLGG GCALLRCIPA

Consensus           VAV-K-G--- -VE--E-K-R --DA-----A AVEEGIV-GG G--LL---P-
                         |63 (373-388 AA)|

424                                                           472
HSP 65 - M.T.       LDELK.LEGD EATGANIVKV ALEAPLKQIA FNSGLEPGVV AEKVRNLPAG
HSP 60 - RAT        LDSLKPANED QKIGIEIIKR ALKIPAMTIA KNAGVEGSLI VEKILQSSSE
HSP 60 - HUMAN      LDSLTPANED QKIGIEIIKR TLKIPAMTIA KNAGVEGSLI VEKIMQSSSE

Consensus           LD-L-----D ---G--I-K- -L--P---IA -N-G-E---- -EK-------

473                                                           522
HSP 65 - M.T.       HGLNAQTGVY EDLLAAGVAD PVKVTRSALQ NAASIAGLFL TTEAVVADKP
HSP 60 - RAT        VGYDAMLGDF VNMVEKGIID PTKVVRTALL DAAGVAFLLT TAEAVVTEIP
HSP 60 - HUMAN      VGYDAMAGDF VNMVEKGIID PTKVVRTALL DAAGVASLLT TAEVVVTEIP

Consensus           -G--A--G-- ------G--D P-KV-R-AL- -AA--A-L-- T-E-VV---P
                                                        |84 (499-514 AA)|

523        540
HSP 65 - M.T.       EKEKASVPGG GDMGGMDF-- -----
HSP 60 - RAT        KEEKD..PGM GAMGGMGGGM GGGMF
HSP 60 - HUMAN      KEEKD..PGM GAMGGMGGGM GGGMF

Consensus           --EK---PG- G-MGGM---- -----
```

Fig. 1 (continued)

The "Protective" Motif

MT  HSP Peptide 6- (31-46)   G P K G R N V V L E K K W G A P
MT  HSP Peptide 7- (37-52)             V V L E K K W G A P T I T N D G
Rat HSP Peptide 5- (36-55)               T V I I E Q S W G S P K V T K D G V T V Common Motif                          V = = E - - W G - P

Fig. 5

AMINO ACID SEQUENCES, DNA ENCODING THE AMINO ACID SEQUENCES, ANTIBODIES DIRECTED AGAINST SUCH SEQUENCES AND THE DIFFERENT USES THEREOF

RELATED APPLICATIONS

This is a Continuation Application of U.S. application Ser. No. 09/847,637 filed May 2, 2001, now U.S. Pat. No. 6,770,281 which is a continuation-in-part of PCT/IL99/00595, filed Nov. 4, 1999, which claims priority from U.S. Provisional Application No. 60/107,213, filed Nov. 5, 1998.

FIELD OF THE INVENTION

The present invention relates to various peptides, homologous to regions of heat shock protein (HSP), to DNA sequences encoding such peptides, to DNA constructs comprising the DNA sequences, to antibodies directed against peptides of the invention. The invention also relates to active vaccines comprising a peptide, a DNA sequence or a DNA construct of the invention, and to a passive immunization composition comprising at an antibody of the invention.

BACKGROUND

Throughout this application, various publications are referred to by Arabic numerals in parentheses. These publications are incorporated herein in their entireties and constitute part of the description.

Adjuvant Arthritis (AA) is an experimental model of autoimmune arthritis which can be induced in susceptible strains of rats such as inbred Lewis or Wistar strains upon vaccination with heat-killed *Mycobacterium tuberculosis* (MT) in complete Freund's Adjuvant (CFA) [1-3]. The disease cannot be induced in resistant strains of rats (e.g., Brown-Norway; Fisher [5, 6], and Lewis rats develop resistance to re-induction of the disease after recovery from arthritis.

The inventors have previously show that resistance to AA can be transferred to a susceptible strain of rats by intravenous infusion of immunoglobulins from the resistant strains, and that resistance is associated with the presence of antibodies against the 65 kD MT heat shock protein (HSP 65) [4].

Heat shock proteins are a family of highly conserved proteins. There is ~50% amino acid identity between the Mycobacterial HSP 65 and the mammalian HSP 60 [21]. The role of the 65 kD heat shock protein (HSP 65) of MT in the pathogenesis of autoimmune arthritis, both in experimental animals [7, 8] as well as in humans [9-11], has been investigated intensively in the past several years. For example, Barker et al. [32] describe the suppression of arthritogenic immune responses in mice given HSP65 and pristane. The antigen used to elicit the response was full-length HSP65, and no attempt was made to investigate the effect of specific sub-domains or peptides deriving from this protein.

AA can be passively transferred by a T-cell clone reactive to residues 180-188 of the MT HSP 65, and in patients suffering from rheumatoid arthritis (RA), an association between T-cell responses to HSP 65 and early stages of joint inflammation has been found [7, 12-14]. Paradoxically, pre-immunization with the mycobacterial HSP 65 leads to resistance to induction of the disease by MT, and this protective effect is believed to be mediated by T cells specific for HSP 65 [7, 15-16]. Likewise, although arthritic rats develop vigorous T cell responses to self-HSP and to peptide 180-188 of the MT HSP, neither of these is arthritogenic when injected to arthritis-susceptible rats [15, 17]. These results and other suggest that HSP may contain epitopes that are disease-related and other epitopes that confer resistance [5, 19, 20]. Both the pathogenic immune response as well as the protective effect were attributed to anti-HSP T-cells. The following Examples illustrate the fine epitope specificity of the anti-HSP antibodies of arthritis-susceptible and resistant rats.

In addition, the inventors have found that naive Lewis rats lack antibodies to certain epitopes of the mycobacterial HSP 65 which are found naturally in young BN and old naive Lewis rats, and that are acquired by young Lewis rats after recovery from the disease. Analysis of the primary and tertiary structure of the whole MT HSP 65 kD molecule indicated that these "protective" epitopes are potential B-cell epitopes with a non-conserved amino acid sequences that are found on the outer surface of the molecule.

Pre-immunization of Lewis rats with one of the "protective" epitopes prior to induction of the disease induced antibodies against the whole molecule as well as resistance to disease induction. This peptide corresponds also to the self-HSP 60 epitope to which antibodies were found in the arthritis-resistant rats, but not in the arthritis-susceptible naive Lewis rats.

SUMMARY

The present invention relates to a peptide comprising the amino acid sequence substantially as denoted by SEQ ID NO:1 and biologically functional homologues and derivatives thereof.

More particularly, the invention relates to a peptide having the amino acid sequence substantially as denoted by SEQ ID NO:2 and biologically functional homologues and derivatives thereof and to a peptide having the amino acid sequence substantially as denoted by SEQ ID NO:3 and biologically functional homologues and derivatives thereof.

In addition, the invention relates to a peptide comprising the amino acid sequence substantially as denoted by SEQ ID NO:4 and biologically functional homologues and derivatives thereof.

The peptides of the invention can be synthetic peptides and chemically modified peptides.

The peptides of the invention are capable of conferring immunity against autoimmune and/or inflammatory disorders.

In a further aspect, the invention relates to a nucleic acid sequence encoding a peptide of the invention and to DNA constructs comprising the same.

In yet a further aspect, the invention relates to vaccines comprising as active ingredient an effective vaccinating amount of at least one peptide of the invention, or a nucleic acid according to the invention. The vaccines of the invention are particularly useful in conferring immunity against autoimmune or inflammatory disorders.

Still further, the invention relates to antibodies directed against the peptides of the invention and to compositions comprising them. The compositions of the invention are particularly useful for the passive vaccination against autoimmune or inflammatory disorders.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1, *Mycobacterium Tuberculosis*, rat HSP 60 and human HSP 60 (sequences P06806, P19227 and P10809, corresponding to SEQ ID NOs:6, 7 and 8 respectively), were compared with pileup program from GCG-Wisconsin Package v9.0. The conserved regions are indicated (consensus). Bold, underlined residues represent the preferred peptides.

FIG. 5, common motif within peptides 6, 7 and R5, V--E--WG-P (also denoted by SEQ ID NO:9) is shown.

DETAILED DESCRIPTION

Figure 2:
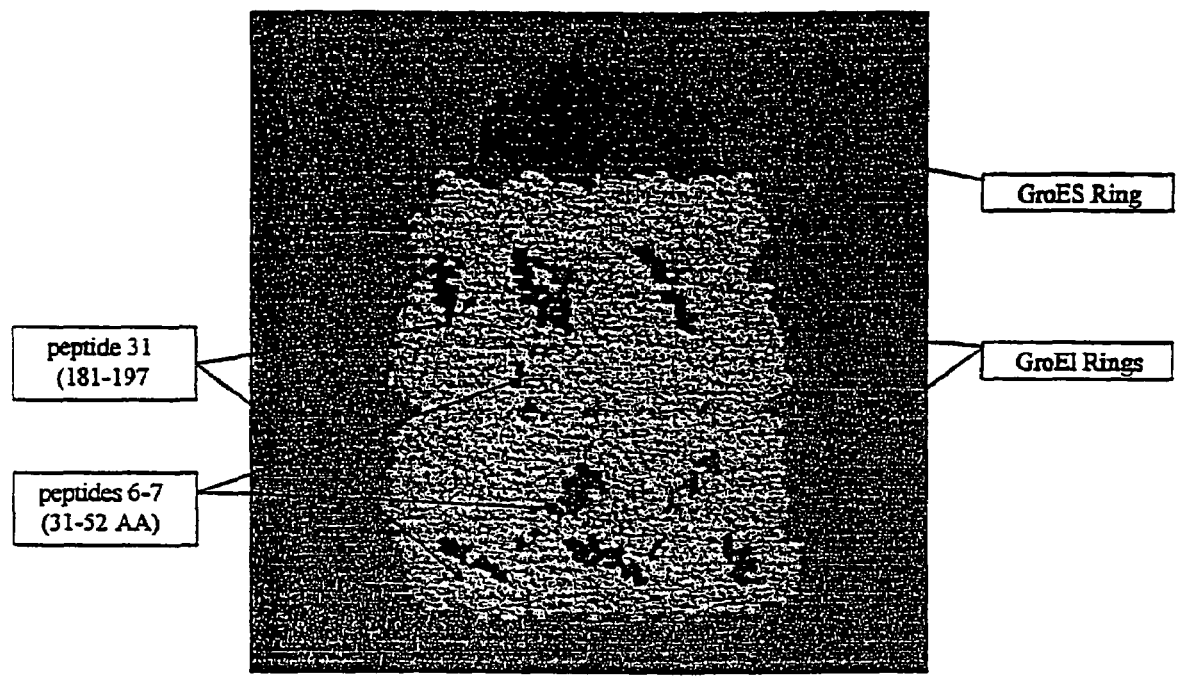
FIG. 2, the GroES heptameric ring is shown in dark gray. The two GroEL heptameric rings are shown in light gray. Peptides 6-7 (amino acids 31-52) and 31 (amino acids 181-197) are also indicated.

The present invention relates to peptides comprising the amino acid sequence substantially as denoted by SEQ ID NO:1, and biologically functional homologues and derivatives thereof.

Preferably, the peptide according to the first embodiment of the invention has the amino acid sequence substantially as denoted by SEQ ID NO:2 or the amino acid sequence substantially as denoted by SEQ ID NO:3.

The invention further relates to a peptide comprising the amino acid sequence substantially as denoted by SEQ ID NO:4 and biologically functional homologues and derivatives thereof.

The invention also relates to a nucleic acid sequence which encodes a peptide according to the invention.

More particularly, the invention relates to a DNA sequence comprising the nucleic acid sequence substantially as denoted by SEQ ID NO:5, and biologically functional derivatives thereof. This nucleic acid sequence encodes a peptide having the sequence substantially as denoted by SEQ ID NO:4.

The amino acid and nucleic acid sequences are presented in Table 1.

TABLE 1

| SEQ ID No | Peptide No. | Amino Acid or Nucleic Acid Sequence |
|---|---|---|
| 1 | | GPKGRNVVLEKKWGAPTITNDG |
| 2 | 6 | GPKGRNVVLEKKWGAP |
| 3 | 7 | VVLEKKWGAPTITNDG |
| 4 | R5 | TVIIEQSWGSPKVTKDGVTV |
| 5 | | GCCGCCATGGGACCAAAGGG ACGCAACGTGGTACTAGAGA AGAAATGGGCGCGCCGT AGCTCGAGA |

By the term "biologically functional homologues and derivatives" is meant any variations, including deletion, substitution and/or insertion of an amino acid residue in the amino acid sequences or a nucleic acid in the nucleic acid sequences of the invention which would not alter the biological activity of the peptides, or peptides encoded by the nucleic acid sequences, against autoimmune diseases. Thus, this term is to be taken to mean peptides with similar structure, peptides or their derivatives that are recognized by the protective antibodies and/or peptides or their derivatives that can induce protective antibodies upon immunization.

The invention further relates to DNA constructs comprising the nucleic acid sequence of the invention or functional homologues and derivatives thereof. The constructs of the invention may further comprise additional elements such as promoters, regulatory and control elements, translation, expression and other signals, operably linked to the nucleic acid sequence of the invention.

The invention also relates to a vaccine comprising as active ingredient an effective vaccinating amount of at least one peptide of the invention. The vaccines of the invention are particularly intended to confer immunity against inflammatory and autoimmune diseases, for example, rheumatoid arthritis or adjuvant arthritis.

By the term "effective vaccinating amount" is meant an amount sufficient to stimulate the immune system, directly or indirectly, and confer immunity against inflammatory and autoimmune diseases. Such effective amount is determined the severity of the disease, age, sex and weight of the patient, as well as the patient's general condition, and by other considerations known to the attending physician. Preferred doses, per injection, may be 0.02-2 mg/Kg body weight.

The vaccines of the present invention may alternatively comprise as the active ingredient at least one nucleic acid sequence according to the invention.

The vaccines according to the invention may optionally further comprise pharmaceutically acceptable carriers, diluents additives, excipients and adjuvants. By the terms "pharmaceutically acceptable carriers, diluents additives, excipients and adjuvants" is meant any inert, non-toxic material that may assist in the efficient delivery of the active ingredient.

The term "antibody" as used in connection with the present invention refers to both polyclonal and monoclonal antibodies. Polyclonal antibodies may be generated in rabbits, chicken, mice, rats, sheep, or similar mammals. The generation of polyclonal antibodies against peptides is described in the above-noted Current Protocols in Immunology, Wiley and Sons Inc. Chapter 9.

Monoclonal antibodies may be prepared from B cells taken from the spleen or lymph nodes of immunized animals, in particular rats or mice, by fusion with immortalized B cells under conditions which favor the growth of hybrid cells. For fusion of murine B cells, the cell line Ag-8 is preferred.

The technique of generating monoclonal antibodies is described in many articles and textbooks, such as the above-noted Chapter 2 of Current Protocols in Immunology. Chapter 9 therein describes the immunization of laboratory animals with peptides. Spleen or lymph node cells of these animals may be used in the same way as spleen or lymph node cells of protein-immunized animals, for the generation of monoclonal antibodies as described in chapter 2 therein.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody.

An antibody is said to be "directed against" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies of the invention may be provided in the form of compositions for use in passive immunization. While such compositions are generally administered by injection, it is not intended that the present invention be limited to this route alone. In general, however, the compositions of the invention are administered by intramuscular or subcutaneous injection. Occasionally, the intravenous or intraperitoneal routes may also be used to administer the compositions of the invention.

In addition to the active ingredient (i.e. the antibody), the compositions of the invention may also comprise a buffering agent, an agent which adjusts the osmolarity thereof, and optionally, one or more further additives, such as carriers, as known in the art.

A preferred buffering agent is phosphate-buffered saline solution (PBS), which solution is also adjusted for osmolarity.

A preferred composition is one lacking a carrier. Such formulations are preferably used for administration by injection, including intramuscular and intravenous injection.

The preparation of pharmaceutical and immunizing compositions is well known in the art and has been described in many articles and textbooks, see e.g., Remington's Pharmaceutical Sciences, Gennaro A. R. ed., Mack Publishing Company, Easton, Pa., 1990.

It has been shown that the development of autoimmune diabetes in the NOD mouse is marked by the presence of T-cells reactive to the p277 peptide of the HSP 60. It has further been shown that the p277 peptide can be used as a therapeutic vaccine to arrest NOD diabetes [28]. The p277 peptide has been shown to arrest also autoimmune diabetes induced by the Streptozotocin toxin [29]. Likewise, the vaccines according to the invention may also be used to suppress an autoimmune disease.

Furthermore, the vaccines of the invention may also be used to prevent relapses of autoimmune diseases, which characterize many autoimmune diseases. Prevention of a relapse is therefore part of the therapeutic approach to these disorders. The above peptide p277 has been shown to prevent NOD mice diabetes by turning off the anti-p277 immunity early in life. It was later shown to arrest autoimmune process even after it is far advanced [28].

Another possibility is that antibodies against the HSP molecule suppress inflammation by inhibiting the proinflammatory effect of the HSP on the innate immune system. Mycobacterial HSP65 has been shown to induce release of pro-inflammatory cytokines from human monocytic cells [18] and the mammalian HSP60 has been shown to synergize with IFN-γ and to promote pro-inflammatory cytokines like IL-12 and IL-15 [31]. Induction of anti-Mycobacterial/anti-self HSP antibodies may suppress those proinflammatory effects.

Specific immunoglobulins (antibodies) are commonly used for prevention and treatment of infectious diseases (i.e. viral hepatitis). This is termed passive vaccination. Immunoglobulins can also be used to suppress or prevent relapses of autoimmune diseases like ITP (Immune Thrombocytopenic Purpura), Myasthenia Gravis (MG), and other autoimmune diseases. [30].

Thus, in yet a further aspect, the invention relates to an antibody directed against at least one peptide according to the invention or functional homologues and derivatives thereof, which can induce the production of said antibody.

The antibodies of the invention may be polyclonal or monoclonal antibodies.

In yet a further aspect, the invention relates to a composition for the passive immunization comprising at least one antibody according to the invention, and may optionally further comprise pharmaceutically acceptable carriers, diluents, additives, excipients and adjuvants. The composition of the present invention is particularly intended for the passive vaccination or immunization against, and treatment of autoimmune or inflammatory disorders, for example, rheumatoid arthritis.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

The following Examples show the anti-MT HSP antibody response of various rats and its correlation with susceptibility to induction of arthritis. Only a limited number of epitopes in the bacterial HSP molecule is recognized by rat antibodies. The repertoire of this antibody differs between resistant and susceptible strains. Resistant strains were found to respond to peptides that are found on the outer surface of the molecule, as well as to the whole molecule. On the other hand, antibodies from naive Lewis rats reacted with a smaller number of peptides, which are less exposed on the outer surface of the molecule and did not react with the intact HSP. The presence of antibodies against some of the epitopes, as well as the whole MT-HSP, may be associated with resistance to the induction of arthritis and they were therefore named "protective" epitopes.

It has been previously reported that the T cell response to bacterial HSP shows determinant spreading. The present data, given in the following Examples, show that there is a clear B cell determinant spreading as well, and this spreading can occur also spontaneously, namely without intentional vaccination. The B cell epitopes, as will be shown, are different from the T cell epitopes. This observation is of particular significance to the present invention.

Young naive Lewis rats recognized only two bacterial epitopes; peptides 40 and 63. Four months Lewis rats recognized, in addition, peptides 6, 36 and 45 and nine months Lewis rats recognized peptides 7 and 31, in addition to all the other mentioned peptides. Recognition of these peptides is also associated with recognition of the whole bacterial HSP molecule.

The B cell epitope repertoire of the young BN rats is similar to that of the old Lewis rats including only one additional peptide, peptide 59. Lewis rats that were immunized with the CFA responded to all the aforementioned peptides, as well as to two additional peptides, namely 21 and 84.

Although all the anti HSP peptide antibodies found in naive old Lewis rats and in naive young BN rats are referred to as natural antibodies, it is possible that they are elicited as a response to the exposure of these rats to environmental pathogens (as "natural" antibodies may indeed always be) and that the epitope spreading in response to these pathogens occurs in the BN rat more rapidly, earlier and in more strongly than in the Lewis rat. Lewis rats have to be immunized with CFA in order to mimic the natural response of the BN rats. The similarity of the antibody repertoire of the naive BN rats to that of the immunized Lewis rat supports this possibility.

The nature of the B cell epitopes and the correlation between recognition of certain epitopes and the whole molecule can be better understood from primary and tertiary structure analysis of the molecule, shown hereafter.

To see whether the anti-HSP protective antibodies can be induced by immunization with the "protective" peptides, Lewis rats were immunized with the various peptides, without Freund's adjuvant. Immunization with three peptides, the bacterial peptides 6 and 7, and the mammalian peptide 5, led to production of antibodies against bacterial peptide 6, as well as to an anti-HSP response, showing that antibodies against an "external" peptide will lead to recognition of the whole molecule. Induction of these antibodies also led to disease resistance.

Although the mechanism of disease resistance induced by the natural as well as the induced anti-HSP antibodies has not been yet clarified, it is possible that the antibodies against the MT HSP inhibit the early steps of induction of pathogenic T cells to the peptide by intervening in the antigen processing or the T cell recognition of the pathogenic epitopes. Alternatively they may prevent the effector steps of the pathogenic response by binding to the self HSP-cross reacting target antigen.

The T cell response of AA susceptible Lewis and AA resistant WKA Wistar rats to the bacterial HSP 65 kD has been thoroughly studied. It has been shown that in the early post immunization stages the Lewis T cells respond to several determinants found in the N terminal, as well as in the carboxy terminal of the molecule, whereas later a shift to carboxy terminal epitopes has developed. The early T cell response of Wistar rats was similar to that of the late response of the Lewis rats. As the 3D structure of the molecule does not show the carboxy and the N terminal sites to be in different locations of the molecule, it is not surprising that the B-cell epitopes were found all along the molecule without any selection of either the carboxy or the N terminal of the molecule.

A comparison between the published dominant T cell epitopes and the present B cell epitopes did not reveal common epitopes. To the contrary, the lack of natural antibodies to certain epitopes like 6, 7 or 31 in the naive Lewis rat is associated with an early T cell response to these epitopes, whereas the presence of antibodies to epitopes like 40 and 63 is associated with lack of an early T cell response. Based on these correlations, it may be suggested that the presence of natural antibodies to certain epitopes may actually inhibit T cell response to them, whereas the lack of antibodies enables the T cells to respond to these epitopes. For example, AA susceptible Lewis rats that do not have natural antibodies to the bacterial peptide 31 can develop a T cell response to this peptide, and these pathogenic T cells can induce arthritis.

As previously mentioned, there was a clear correlation between disease resistance and the presence of anti-HSP antibodies. Young naive Lewis rats did not have detectable antibodies against the HSP molecule whereas nine months old Lewis rats developed these antibodies in a significant titer. Parallel to the development of the anti-HSP response, the old rats also became resistant to induction of arthritis. Young Lewis rats acquired both the antibodies and disease resistance after immunization with CFA and the naturally resistant BN rats had anti HSP antibodies spontaneously, without the need for immunization. It is possible therefore that these antibodies bind the bacterial HSP immediately after immunization and prevent it from becoming accessible to the cellular arm of the immune system.

As noted previously, the epitopes "chosen" by the B cells from the bacterial HSP are epitopes that have relatively little homology with the self HSP, most probably as a result of tolerance to self antigens.

Analysis of the anti self (rat) HSP antibody repertoire indeed showed that there is a limited number of epitopes recognized by the rat immunoglobulins in the self HSP molecule. Naive young Lewis rats did not respond to any self peptide neither did they respond to the whole self HSP 60 molecule. BN and post-AA Lewis rats that reacted with 8-10 bacterial HSP epitopes responded to only two epitopes in the self HSP, peptides M5 and M30, as well as to the whole self HSP molecule.

Expression of the mammalian (or self) HSP is upregulated in inflamed synovia of rats with AA [22] and cross-reactive immune recognition has been found between the Mycobacterial HSP 65 kD and endogenous self HSP 60 kD at the T-cell level [23-25].

As the anti self antibodies were found only in the resistant rats, it is possible that antibodies that cross react with the self HSP may conceal it from the pathogenic T cells and thus act as protective antibodies.

It is interesting to note that one of the two self protective epitopes is the self peptide 5, which is the homologous rat epitope to the bacterial protective peptide 6. Moreover, immunization with the bacterial peptides 6 and 7 and with the mammalian peptide 5 led to the production of anti bacterial HSP 6 and anti bacterial HSP antibodies, as well as protection against disease induction. Observing the primary structure of these three peptides leads to the conclusion that they express a common motif (V—E—W G—P, as denoted by SEQ ID NO:9) which might be the protective motif of these peptides (FIG. 5).

Therefore, the humoral immune response to the bacterial HSP may be aimed at a limited number of potential B-cell epitopes. These epitopes are peptide stretches located between amino acids that serve as bends and spacers, and are found in non-conserved parts of the molecule. Recognition of B-cell epitopes that are exposed on the surface of the molecule leads to binding to the whole molecule and is associated with resistance to induction of arthritis.

This resistance occurs naturally in some strains of rats whereas in others it can be acquired with age or upon immunization with HSP. Immunization with some of the "protecting" epitopes can lead both to disease resistance as well as to the serological profile that is present in the resistant strains.

The present invention can also provide a method for the prediction of susceptibility/predisposition to develop autoimmune arthritis. In the rat system, it has been shown that naive young Lewis rats do not have antibodies against peptide 6 of the HSP, and that they are susceptible to the development of arthritis after exposure to or immunization by HSP. In a similar manner, healthy individuals that lack sub-groups of antibodies against HSP specific peptides may be susceptible to onset of arthritis. The present invention also provides an assay for the assessment and determination of susceptibility/predisposition to arthritis. The assay can be performed by ELISA, in which the peptides will be bound to the solid phase and serum samples added, followed by adding anti human Igs. Other known immunological analysis techniques can also be used.

The invention will be described in more detail on hand of the following examples, which are illustrative only and do not limit the invention thereto.

EXAMPLES

Materials

Animals:

Female inbred Lewis rats, 6 weeks or 9 months old, were obtained from Harlan Lab. Israel. Female Brown-Norway (BN) rats, 6 weeks old, were obtained from Harlan Sprague-Dawley, USA.

Antigens and antibodies:

Recombinant HS P65 of *Mycobacterium Tuberculosis* was a gift from Dr. M. Singh (The WHO Recombinant Protein Bank, Germany). Recombinant mammalian HSP 60 was purchased from StressGen Biothec. Corp. (Victoria, BC, Canada). Synthetic peptides of MT HSP 65 were a gift from Dr. L. Adorini (The Roche Milano Ricerche, Milano, Italy). Synthetic peptides of the mammalian HSP 60 were a gift from Dr. I. Cohen (The Weizmann Institute, Rehovot, Israel). Goat anti Rat IgG conjugated to alkaline-phosphatase was purchased from Jackson ImmunoResearch Lab. Inc. (Avonsdale, Pa.).

Methods

Induction and Clinical Assessment of Adjuvant Arthritis:

Lewis rats were injected with 1 mg of *Mycobacterium Tuberculosis* H37Ra (Difco, Detroit, Mich.) in Complete Freund's Adjuvant (Difco) subcutaneously at the base of the tail. Severity of Arthritis (arthritis index) was assessed blindly as follows: 0—no arthritis; 1—redness of the joint; 2—redness and swelling of the joint. The ankle and tarsal-metatarsal joints of each paw were scored. A maximum score of 16 can be obtained, but a score above 8 indicates a severe disease.

Dot Blots assay:

Antigens were dissolved in PBS and samples of 1 µg were adsorbed on Nitrocellulose paper. The paper was air-dried and incubated with BSA 1% in PBS for 20 min. to block non-specific binding. The samples were then washed in PBS-Tween 0.05% and incubated with rat sera diluted 1:100 in BSA-PBS, for 90 min. at room temp. Samples were washed and incubated with goat anti rat antibody conjugated to alkaline phosphatase diluted 1:1000 in BSA-PBS for 90 min. at RT. After re-washing the color reaction was developed by adding a mixture of BCIP-NBT (Sigma-Fast, Sigma) to the cells for 15 min. The reaction was stopped by the addition of tap water.

ELISA:

Flat-bottomed 96 well plates (Corning) were coated with mammalian HSP 60, or Mycobacterial HSP 65 (10 µg/ml) in carbonate buffer pH 9.6 overnight at 4° C.

After extensive washing with PBS-Tween 0.05% plates were incubated with blocking buffer containing 1% BSA (Sigma) for 60 min. at RT.

HSP peptides were attached to plates pre-treated with glutaraldehyde according to Kasprzyk et al. [26]. Shortly, plates were coated with 100 µl/well of 5% w/v of glutaraldehyde in PBS for 1 hour at room temp. Plates were washed thoroughly with PBS and peptides (1 µg/100 µl) were added to each well, incubated overnight at 4° C. Plates were shaken dry and blocked with BSA 1% in PBS.

Plates coated with either HSP or peptides were washed again and incubated with rat sera diluted 1:100 with PBS-Tween 0.01% for 90 min. at room temp. After re-washing the plates were incubated with Goat anti rat IgG or IgM conjugated to alkaline-phosphatase for 60 min. at room temp. The presence of antibodies was revealed by addition of the substrate PNP (NP 100, Chemicon, Temecula, Calif.) to the plates. Optical density was measured photometrically at 405 nm.

Amino Acid Comparison:

"Pileup" and "pretty" programs (GCG—Wisconsin package, v.9.0) were used to compare amino acid sequences of three HSP 60 (*Mycobacterium Tuberculosis*, rat and human).

Structure Analysis:

RasMol v. 2.6 program and the 3D structure of the *E. coli* complex GroEL-GroES (pdb ID: 1 AON reference) were used to analyze the position of epitopes.

Since the crystal structure of MT HSP 65 kD is not yet completely known, a three-dimensional model for the tertiary structure of MT HSP 65 kD based on the solved crystal structure of GroEL from *E. coli* (pdb ID: 1 GRL) was used as template. This model was built by programs for comparative protein modeling.

Modulation of AA by mycobacterial and mammalian HSP peptides:

HSP 65 derived peptides were tested for their ability to modulate the appearance or severity of AA in Lewis rats. Rats were immunized with 100 µg of each peptide in PBS, three weeks (3W), 2W and 1W before induction of AA by MT. Control rats received PBS. Rats were bled for testing antibody presence before injection of MT and 30 days post MT injection.

Figure 6:
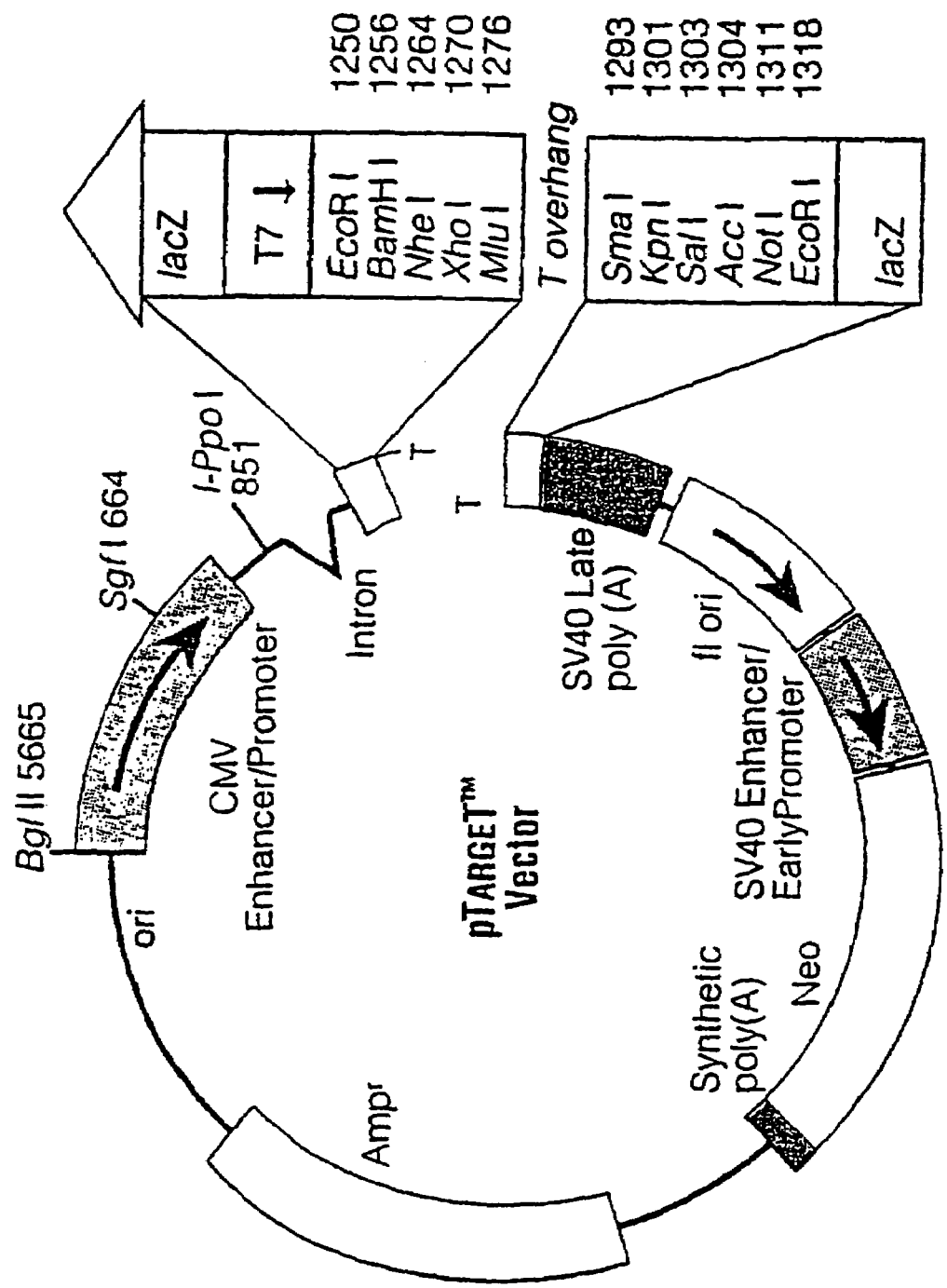
FIG. 6, restriction map of the plasmid pTARGET is shown.

DNA Vaccine preparation:

A synthetic oligo DNA, having the SEQ ID NO: 5, encoding the oligopeptide *Mycobacterium Tuberculosis* HSP 65 kD No. 6, presented in Table 1, was cloned into the commercially available mammalian expression vector, pTARGET (Programa, Madison, Wis., USA), having the restriction map depicted in FIG. 6. The cloning was carried out according to the manufacturer's instructions.

The plasmid construct was then transferred into *E. coli* JM 109 strain and expanded to large scale for further plasmid purification, using the DNA purification system Wizard Plus Maxipreps kit (Programa, Madison, Wis., USA).

Animal vaccination:

Lewis rats were pre-treated with Bupivaccine (Astra) two days prior to vaccination and later disease induction. The rats were then twice injected with 100 µg of the DNA construct, into the tibialis anterior muscle, with a week interval between the injections.

Results

The Interaction of Rat Ig with Whole Mycobacterial HSP 65 and its Peptides

Previous experiments conducted by the inventors showed that Ig's from AA resistant naive rats (i.e. BN or Fisher) as well as Lewis rats that recovered from AA (post AA Lewis rats), were able to suppress the induction of AA in naive Lewis rats and bound to the bacterial HSP 65 in a dot blot assay. To obtain a more quantitative evaluation of this binding, the interaction of Ig's from these rats with the whole molecule of the Mycobacterial HSP 65, known to be associated with AA in Lewis rats, was tested by Dot-Blot and ELISA.

It was found that Ig's from 6-8 week old BN rats, and post AA Lewis rats, reacted strongly with the HSP while no reaction was found when Ig's from naive Lewis rats were tested. Interestingly, it was found that Ig's from nine months old naive Lewis rat also reacted with the HSP.

To define the epitopes recognized by the anti bacterial HSP antibodies, the inventors tested by Dot-Blot the interaction of Ig's from naive young BN rats and post AA Lewis rats with 90 16-mer synthetic peptides of the Mycobacterial 65 kD HSP. Ig's from naive young Lewis rats served as control.

Only 10 peptides out of the 90 peptides tested (Table 2) reacted with the immunoglobulins tested. All of the rats immunoglobulins reacted with two peptides: 40 (residues 235-250) and 63 (residues 373-388). When these rats age, they acquire antibodies against additional peptides, and a similar profile to that of old Lewis rats is found in young naive BN rats, and Lewis rats that were immunized with CFA reacted also with peptides 21 (residues 121-136) and 84 (residues 499-514). It is noted that although naive Lewis rats do not recognize the whole molecule of HSP 65 kD, its Ig's can interact with certain peptides of this molecule, without any effect on susceptibility to AA.

from naive and post AA Lewis rats as well as from naive BN rats to whole mammalian HSP 60 was tested by ELISA.

The results presented in Table 3 indicate that that naive and four months old Lewis rats do not possess anti self-HSP 60 antibodies, whereas nine months old Lewis rats, young BN rats and post-AA Lewis rats had significant binding to the self-HSP (Table 3). Some naive Lewis rats had very low concentrations of the antibodies.

TABLE 3

Antibodies to Mammalian HSP 60 Peptides

| Strain | Peptide Sequence | | | Disease Susceptibility |
|---|---|---|---|---|
| | M 5 61-80 | M 30 436-455 | M-HSP 60 | |
| Lew-6w | − | − | − | 8/10 |
| Lew-4m | − | − | − | 3/3 |
| Lew-9m | ++ | ++ | + | 0/7 |
| BN-6w | + | + | + | 0/10 |
| Lew-Post AA | +++ | ++ | + | 0/10 |

O.D.: <O.15 = −;
0.16-0.45 = +;
0.46-0.75 = ++;
>0.75 = +++

Immunoglobulins from naive Lewis and BN rats and post-AA Lewis rats were tested for binding to 38 synthetic 20-mer peptides of the mammalian HSP 60 by Dot-Blot. It was found that Ig's derived from BN and post-AA Lewis rats, but not from naive Lewis rats, reacted with 2 peptides only: peptide 5 (residues 61-80) and peptide 30 (residues 436-455). Quantitative analysis of this binding as well as the binding of immunoglobulins from four and nine months old Lewis rats confirmed the dot blot findings (Table 3).

TABLE 2

Antibodies to Mycobacterial HSP 65 Peptides

| Strain | 21<br>121-136<br>SEQ ID #10 | 84<br>499-514<br>SEQ ID #17 | 59<br>349-364<br>SEQ ID #15 | 7<br>37-52<br>SEQ ID #3 | 31<br>181-196<br>SEQ ID #11 | 6<br>31-46<br>SEQ ID #2 | 36<br>211-226<br>SEQ ID #12 | 45<br>265-280<br>SEQ ID #14 | 40<br>236-251<br>SEQ ID #13 | 63<br>373-388<br>SEQ ID #16 | Disease HSP 65 | Susceptibility |
|---|---|---|---|---|---|---|---|---|---|---|---|---|
| Lew-6w | − | − | − | − | − | − | − | − | + | + | − | 8/10 |
| Lew-4m | − | − | − | − | − | + | + | + | + | + | − | 3/5 |
| Lew-9m | − | − | − | + | ++ | + | + | + | ++ | +++ | + | 0/7 |
| BN-6w | − | − | + | + | + | + | ++ | + | ++ | + | +++ | 0/10 |
| Lew-Post AA | + | + | +++ | + | ++ | +++ | +++ | ++ | ++ | ++ | ++ | 0/10 |

O.D: <O.15 = −;
0.16-0.45 = +;
0.46-0.75 = ++;
>0.75 = +++

Binding of Rat Ig's with the Mammalian HSP 60 and its Peptides

Previous studies have shown that certain bacterial HSP peptides may trigger self HSP reactive T-cells with disease suppressive regulatory potential. To analyze the anti self-HSP antibody repertoire of these rats, the reactivity of Ig's

Amino Acid Comparison

The HSP 60 family is highly conserved: MT-HSP 65 and its mammalian homologues (rat or human) show 48% identity. In FIG. 1, the three amino acid sequences of the MT-HSP 65, HSP 60 from rat and human are compared. The consensus sequence of these three proteins is shown too. The epitopes that were found to be relevant in this study are shown in Bold and Underlined.

3D Structure Analysis

Tertiary structure plays an important role for B-cell epitope recognition. In a first approach, a simple computer program was provided, that could predict where to find potential B-cell epitopes by screening the primary structure of the peptide. The algorithm is based on a previous analysis by Warren et al. [27] of the Myelin Basic Protein to locate potential epitopes for B-cell. According to their analysis, two sorts of amino acids can be defined:

"Molecular spacers": These are short-chain residues (side chains of one carbon or less) that could provide a molecular gap for adjacent long-chain amino acids. Three amino acids that fit this definition are: Glycine (G), Alanine (A) and Serine (S).

"Molecular bends": Proline (P) residues that can cause disruptions in secondary structure.

Figure 3A:
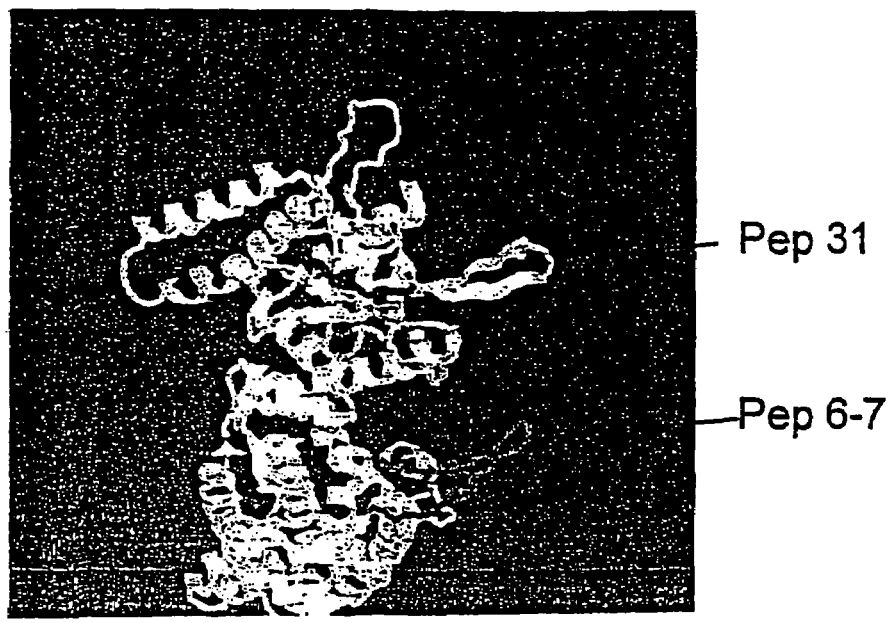
FIGS. 3a-3b, the location of peptides 6, 7 and 31 in the HSP 65 monomer is indicated in a secondary structure configuration (FIG. 3a) and in the space filling mode (FIG. 3b).
Figure 3B:
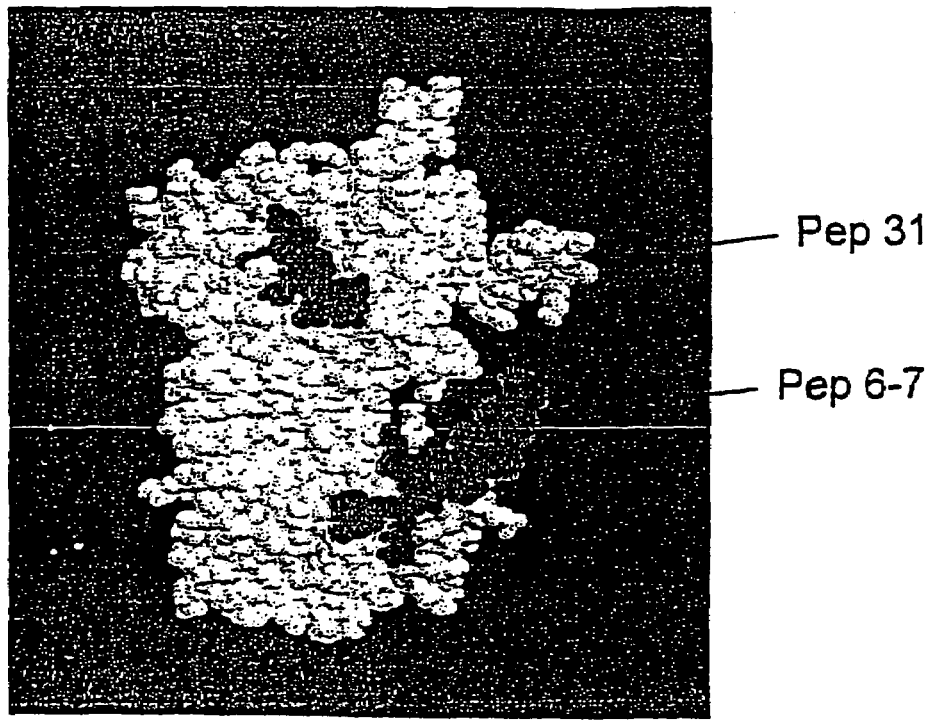

A minimal length of 9 residues for these potential epitopes was set. Following these rules, six series of consecutive long-chain residues (side chains of two carbons or more) located between molecular spacers and/or molecular bends were found (Table 4).

model for the tertiary structure of MT HSP 65 kD based on the crystal structure of E. coli GroEL (FIG. 3) was used.

Structure analysis confirmed that the experimentally recognized epitopes located on the surface of the protein can provide a potential site to antibodies binding. Peptides 6, 7, 21, 31, 59 were those that were found to be the most exposed whereas peptides 36, 40, 45, 63 and 84 are partially exposed.

The single potential epitope that was not recognized experimentally (residues 318-331) seems to be "buried" in the molecule.

Although there is a marked homology between MT HSP 65 kD and mammalian HSP 60 kD, most of the peptides that were found to be recognized by the anti-MT HSP 65 antibodies did not show high residues homology with the mammalian HSP. This may be due to the tolerance to self, that protects the rats from developing an autoimmune autoantibody response to their own HSP 60. Two peptides, 6 and 45, did not seem to conform to this rule as they had sites showing high homology to the self HSP.

These findings may be explained for both peptides as follows:

TABLE 4

Potential epitopes of MT HSP 65 kD

| Location of the peptide (aa residues) | Sequence of the peptide | Length | SEQ ID No. | Experimental peptide matching |
|---|---|---|---|---|
| 35-43 | G-RNVVLEKKW-G | 9 | 18 | 6, 7 |
| 123-132 | A-VEKVTETLLK-G | 10 | 19 | 21 |
| 135-143 | A-KEVETKEQI-A | 9 | 20 | 21 |
| 319-332 | RKVVVTKDAETTIVE | 14 | 21 | none |
| 357-367 | S-DYDREKLQERL-A | 11 | 22 | 59 |
| 383-396 | A-TEVELKERKHRIED-A | 14 | 23 | 63 |
| 183-195 | G-LQLELTEGMRFDK-G | 13 | 24 | 31 |
| 259-270 | S-TLVVNKIRGTFK-S | 12 | 25 | 45 |

The peptide was screened by a computer program and consecutive long-chain residues (side chains of two carbons or more) located between molecular spacers and/or molecular bends are shown (the 6 first peptides). The two peptides below them are the consecutive chain that contain at most one molecular spacer (glycine).

Five of six series that were identified by these rules fit amino acid sequences that were found to be experimentally recognized by B-cell antibodies (Table 1) Consequently, in order to find more epitopes, the program was run with a slight change, namely search of epitopes that contain at most one molecular spacer (G, S or A). The minimal length was set at 12 residues (instead of 9 previously) in order to lower the background (i.e., a penality of three residues was set to compensate the gap). Two new sequences were identified, that were also found to be experimentally recognized by B-cell antibodies (31, 45; see Table 1). The molecular spacer was glycine in these two cases.

In order to better understand the implications of the tertiary structure of MT HSP 65 kD and to locate these different amino acid sequences on the whole molecule, a As to peptide 6 (residues 31-46): antibodies were found to bind peptide 7 (residues 37-52) which overlap the polymorphic part of this peptide, but not peptide 5 (residues 25-40) representing the region homologous with the mammalian HSP. It seems therefore, that these antibodies are directed against the polymorphic (non-self) region of peptide 6 (residues 40-46). It can also provide a hypothesis concerning the "protective" ability of this peptide, partial homology to the mammalian HSP 60 sequence may be responsible for this protective effect.

As to peptide 45 (residues 265-280): This peptide can be divided into two consecutive regions: one polymorphic (residues 265-271) and the second highly conserved (residues 271-280). Analysis of the three-dimensional structure shows that the polymorphic region is the exposed region, whereas the conserved region seems to be "buried" in the whole molecule (not shown). Therefore, it is possible that the antibodies that bind peptide 45 are mainly directed against the exposed polymorphic region.

No particularity concerning the secondary structure and the repartition of hydrophobic/polar residues in these epitopes was noticed (both experimentally and computer recognized). Generally, the experimentally recognized epitopes tend to be hydrophobic (9-12 hydrophobic residues out of 16), but for peptide 59 that is highly polar (13 residues out of 16).

With reference to the Figures, FIG. 2 shows the location of bacterial peptides 6, 7 and 31 on the three dimensional structure of the *E. Coli* GroEL-GroES complex and FIG. 3, as stated, shows the same peptides on a model of the MT HSP 65 based on the structure of GroEL *E. Coli* with a space-filling and secondary structure representations.

Analysis of the Ability of Peptides to Immunize Against AA

To test whether active immunization with bacterial or mammalian HSP peptides that are recognized by protective immunoglobulins can induce protection against AA, Lewis rats were immunized with the mycobacterial peptides 6, 7, 21, 31, 36, 45, 84, that bound antibodies from resistant Lewis rats ("protective" peptides), with some non-reactive mycobacterial HSP 65 peptides: peptide 26 (residues 151-166), 28 (residues 163-178) or peptide 70 (residues 415-430), and with the mammalian peptide 5.

Rats were injected 3 times intraperitoneally (IP), with one week intervals between injections before induction of AA with MT.

Figure 4:
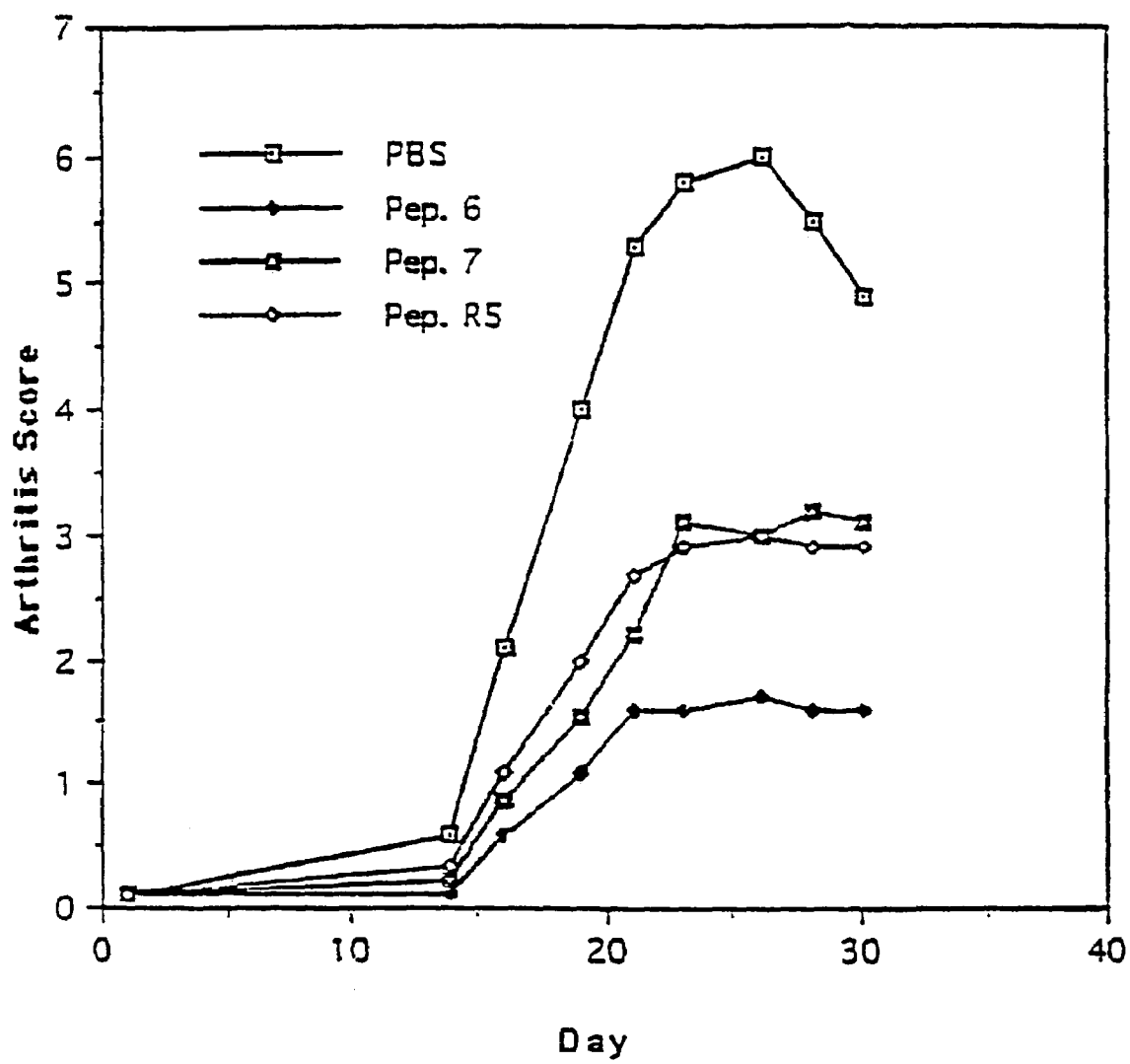
FIG. 4, vaccination against AA with HSP peptides 6, 7 and R5 is shown. PBS was employed as a control.

FIG. 4 shows that only pre-immunization of rats with the bacterial peptides 6 and 7 and the mammalian peptide 5 resulted in a significant suppression of disease severity.

Immunization with these "protective" peptides also resulted in the production of antibodies against peptide 6 as well as against the whole MT HSP 65 (Table 5).

BIBLIOGRAPHY

1. Pearson, C.M., Proc. Soc. Exp. Biol. Med. 91:95-101 (1956)
2. Pearson, C.M. & Wood, F.D., Arthritis Rheum. 2:440 (1959)
3. Waxman, B.H. and Wemersten, C., 1. Arch. Allergy 23:129 (1963)
4. Ulmansky, R., et at., Eur. J. linmunol. 25:952-957 (1995).
5. Hogervorst, E.J.M., et at. Eur. J. Immunol. 21:1289-1296 (1991)
6. Griffiths, M.M., et at., Arthritis Rheum. 36:254 (1993)
7. Van Eden, W., et at., Nature (Lond.) 33 1:171-173 (1988)
8. Holoshitz, J., et at., Science (Wash. DC) 219:56-58 (1983)
9. Holoshitz, J., et at., Lancet 2:305-309 (1986)
10. Res, P.C.M., et at., Lancet 2:478-480 (1988)
11. Gaston, J.S.H., etal., J. Immunol. 143:2494-2500 (1984)
12. Gaston, J.S.H., et at., J. Exp. Med. 171:831-841 (1990)
13. Quayle, A.J., etat., Eur. J. Immunol. 22:13 15-1322 (1992)
14. Henwood, J., et at., Eur. J. Immunol. 23:1256-1265 (1992)
15. Billingliam, M.E.J., etal., J. Exp. Med. 171:339-344 (1990)
16. Hogervorst, E.J.M., et at., mt. Immunol. 4:719 (1992)
17. Young, X.D., et at., Clin. Exp. Immunol. 81:189-194 (1990)
18. Friedland, J.S., etal., Clin. Exp. Immunol. 91: 58-62 (1993)
19. Anderston, S.M., et at., J. Immunol. 152:3656-3664 (1994)
20. Moudgil, K.D., et at., J. Exp. Med. 185:1307-1316 (1997)
21. Jindal, S., et at., Mol. Cell. Biol. 9:2279-2283 (1989)
22. Kleinau, S.K., et at., Scand. J. Immunol. 33:195-202 (1991)
23. Munk, M.E., et at., J. Immunol. 143:2844 (1989)
24. Anderston, S.M., et al., Eur. J. Immunol. 23:33 (1993)
25. Shinnik, T., etal., Eur. J. Irnmunol. 22:1315-1322 (1992)
26. Kasprzyk, P.G., et al., Anal. Biochem. 174:224 (1988)
27. Warren, K.G., et al., Proc. Nati. Acad. Sci. USA 92:11061(1995)
28. Elias, D., et al., Lancet 343:704-706 (1994)
29. Elias, D., et al., Diabetes 45:1168-1172 (1996)
30. Jordan, S.C. and Toyoda, M., Clin. Exp. Immunol. 97:31-38 (1994)
31. Chen, W., etal., J. Immunol 162:3212-3219 (1999)
32. Barker et al., Autoimmunity 14:73-77, (1992)

What is claimed is:

1. A B cell epitope synthetic peptide consisting of the amino acid sequence as denoted by SEQ ID NO:4.

2. The B cell epitope peptide as claimed in claim 1, capable of significantly suppressing disease severity of arthritis.

3. A vaccine for significantly suppressing disease severity of arthritis comprising, as an active ingredient, an effective vaccinating amount of at least one B cell epitope peptide consisting of the amino acid sequence as denoted by SEQ ID NO:4.

* * * * *

SEQUENCE LISTING

```
<160> NUMBER OF SEQ ID NOS: 5

<210> SEQ ID NO 1
<211> LENGTH: 22
<212> TYPE: PRT
<213> ORGANISM: Mycobacterium tuberculosis

<400> SEQUENCE: 1

Gly Pro Lys Gly Arg Asn Val Val Leu Glu Lys Lys Trp Gly Ala Pro
1               5                   10                  15

Thr Ile Thr Asn Asp Gly
            20

<210> SEQ ID NO 2
<211> LENGTH: 16
<212> TYPE: PRT
<213> ORGANISM: Mycobacterium tuberculosis

<400> SEQUENCE: 2

Gly Pro Lys Gly Arg Asn Val Val Leu Glu Lys Lys Trp Gly Ala Pro
1               5                   10                  15
```

```
<210> SEQ ID NO 3
<211> LENGTH: 16
<212> TYPE: PRT
<213> ORGANISM: Mycobacterium tuberculosis

<400> SEQUENCE: 3

Val Val Leu Glu Lys Lys Trp Gly Ala Pro Thr Ile Thr Asn Asp Gly
1               5                   10                  15

<210> SEQ ID NO 4
<211> LENGTH: 20
<212> TYPE: PRT
<213> ORGANISM: Rattus norvegicus

<400> SEQUENCE: 4

Thr Val Ile Ile Glu Gln Ser Trp Gly Ser Pro Lys Val Thr Lys Asp
1               5                   10                  15

Gly Val Thr Val
            20

<210> SEQ ID NO 5
<211> LENGTH: 67
<212> TYPE: DNA
<213> ORGANISM: Mycobacterium tuberculosis

<400> SEQUENCE: 5
gccgccatgg gaccaaaggg acgcaacgtg gtactagaga agaaatgggg cgcgccgtag      60
ctcgaga                                                               67
```